(12) United States Patent
Homer

(10) Patent No.: US 12,102,453 B1
(45) Date of Patent: Oct. 1, 2024

(54) MEANS AND METHOD FOR REDUCING LOWER BODY EXTREMITY INJURIES

(71) Applicant: Von M Homer, Middletown, DE (US)

(72) Inventor: Von M Homer, Middletown, DE (US)

(73) Assignee: Von M. Homer, Middletown, DE (US)

( * ) Notice: Subject to any disclaimer, the term of this patent is extended or adjusted under 35 U.S.C. 154(b) by 383 days.

(21) Appl. No.: 17/179,840

(22) Filed: Feb. 19, 2021

(51) Int. Cl.
| | |
|---|---|
| *A61B 5/00* | (2006.01) |
| *A61B 5/11* | (2006.01) |
| *A61B 5/22* | (2006.01) |
| *A61B 5/397* | (2021.01) |
| *G16H 10/60* | (2018.01) |
| *G16H 40/67* | (2018.01) |
| *G16H 50/30* | (2018.01) |
| *G16H 50/70* | (2018.01) |

(52) U.S. Cl.
CPC .............. *A61B 5/7275* (2013.01); *A61B 5/11* (2013.01); *A61B 5/224* (2013.01); *A61B 5/397* (2021.01); *A61B 5/4528* (2013.01); *A61B 5/486* (2013.01); *A61B 5/7267* (2013.01); *G16H 10/60* (2018.01); *G16H 40/67* (2018.01); *G16H 50/30* (2018.01); *G16H 50/70* (2018.01)

(58) Field of Classification Search
CPC ......... A61B 5/11; A61B 5/7275; A61B 5/224; A61B 5/397; A61B 5/4528; A61B 5/486; A61B 5/7267; A61B 5/1121; A61B 5/1122; A61B 5/4595; A61B 5/586; G16H 10/60; G16H 40/67; G16H 50/30; G16H 50/70

See application file for complete search history.

(56) References Cited

U.S. PATENT DOCUMENTS

| | | | |
|---|---|---|---|
| 11,389,083 B2 * | 7/2022 | Bansbach | ............... A61B 5/744 |
| 2006/0030793 A1 * | 2/2006 | Granata | ............... A63B 26/003 |
| | | | 600/595 |
| 2017/0000386 A1 * | 1/2017 | Salamatian | ............ G16H 10/60 |
| 2020/0029882 A1 * | 1/2020 | Gong | .................... A61B 5/1118 |

* cited by examiner

*Primary Examiner* — Devin B Henson

(57) ABSTRACT

The utilization of sensors towards the study of internal and external work at the distal lower extremity during movement is presented. Inertial Measurement Units (IMUs) and Electromyography (EMG) sensors are paired together to calculate the neuromuscular effort and torque at the ankle and are compared with plantar pressure and torque measurements using the pressure mat. Subsequently image tracking data is also to inform machine learning models that predict real-world distance movement from video recorded movement. Finally, a mobile application is developed allowing users to see a simulation of their movements, among other information.

20 Claims, 8 Drawing Sheets

MEANS AND METHOD FOR REDUCING LOWER BODY EXTREMITY INJURIES

CROSS-REFERENCE TO RELATED APPLICATION

This application claims the benefit of U.S. Provisional Patent Application No. 62/951,969, filed Dec. 20, 2020, which is incorporated by reference herein in its entirety.

TECHNICAL FIELD

The present invention relates generally to orthopedics, and more specifically, a means and method for reducing the risk of distal lower extremity injuries.

BACKGROUND

Lower extremity injuries make up more than 50 percent of injuries amongst athletes. The majority of all lower extremity injuries are ankle injuries and ligament sprains, but may also include medial gastrocnemius injuries to the calf muscle. These injuries have an immediate impact of the natural gait of the injured individual. The muscles in the body contract in different ways to move and help stabilize specific body segments. An individual's natural gait is complete with "shock absorption" to transfer and translate energy that is generated by the muscles and then reflected from the ground back to the body. The energy that is reflected off of the ground is then translated into various forms of energy (i.e., heat and force) which is then processed by the various layers of tissue and muscles that affect and influence movement throughout the joints of the lower extremity. Changes in the alignment of the body through the feet impacts the efficiency of movement. Lower extremity injuries disrupt this influence movement and, often times, it is never fully recovered, and the individual's gait is compromised resulting in diminished athletic performance.

Quantifying neuromuscular effort is very useful in determining an individual's inclination to injury. There is general agreement in the field of the art both extrinsic and intrinsic factors play a role in determining an individual's inclination to injury, specifically, lower body extremity injury. Extrinsic risk factors include, but are not limited to, the level of competition, skill level, shoe type, ankle bracing, and playing surface. Intrinsic risk factors include, but are not limited to age, gender, phase of menstrual cycle (females only), previous injury and inadequate rehabilitation, body size, limb dominance, flexibility (inclusive of generalized joint laxity, ankle and knee laxity, muscle tightness, range of motion), limb girth, muscle strength, postural stability, anatomical alignment, foot morphology, and aerobic fitness.

Traditionally, orthopedic research, clinicians, and athletic trainers have sought ways to reduce the risk of lower extremity injuries by gaining a better understanding of foot function. There are several validated performance tests known in the art including the Rootion Theory, the Tissue Stress Theory, and the Preferred Movement Pathway Theory. The Rootian Theory is a systematic classification of the foot function and foot pathologies based on alignment and calls for using orthotics to adjust an abnormal alignment to prevent and treat foot injuries. The Tissue Stress Theory places emphasis on the pathological magnitudes of stress acting within the structural components of the foot and lower extremity. Conversely, the Preferred Movement Pathway Theory places emphasis on the impact of both alignment and stress in the function of the distal lower extremity to allow the musculature to move in its preferred path. Unfortunately, while widely accepted, these theories do not determine internal and external muscle effort and joint torque and displacement for the purpose of measuring the risk of lower extremity injury.

Attempts have been made, although unsuccessfully, to solve this problem. One illustrative attempt can be seen with respect to U.S. Pat. No. 7,582,064 B2, which generally discloses a system and method for foot assessment. While this disclosure generally teaches to a method for assessing foot displacement and the associated correlation to one's propensity for lower extremity injury, the disclosure does not do not determine internal and external muscle effort and joint torque and displacement for the purpose of measuring the risk of lower extremity injury.

Another attempt can be seen with respect to U.S. Pat. No. 9,829,493 B2, which generally discloses a method and apparatus for the assessment of risk for joint injury. Although this disclosure generally teaches to test kits and methods for identifying methods to permit intervention to reduce the risk of joint injury, this disclosure emphasizes biomechanical movement patterns and does not determine internal and external muscle effort and joint torque and displacement for the purpose of measuring the risk of lower extremity injury.

Yet another attempt can be seen with respect to U.S. Pat. No. 6,192,329 B1, which generally discloses a method and apparatus for assessing risks of injury in children. While this disclosure does consider computer ad physical anatomical models to assess the risk of injury, the disclosure does not do not determine internal and external muscle effort and joint torque and displacement for the purpose of measuring the risk of lower extremity injury.

Other disclosures such as U.S. Pat. No. 9,008,784 A1 and U.S. Patent Application No. 2018/0028109 A1, and the like, teach to wearable devices such as knee braces to prevent the risk of lower extremity injury and, in particular, knee injuries. These disclosures, however, are limited in scope to the use of physical devices and do not measure the actual risk of injury.

Various attempts have been made to measure the risk of lower extremity injury, which may be found in the related art, but have been unsuccessful. Therefore, a need exists for a more effective means to determine how efficiently a person maintains neuromuscular stability of the lower extremities within a certain environment (i.e. an orthotic, shoe, brace, or prosthetic) to measure the risk of lower extremity injury.

SUMMARY OF THE INVENTION

It is to be understood that in the present disclosure, all embodiments are provided as illustrative and non-limiting representatives of many possible embodiments. In addition, the terms "is," "can," "will," and the like are used as synonyms for and interchangeable with terms such as "may," "may provide for," and "it is contemplated that the present invention may" and so forth.

Furthermore, all elements listed by name, such as inertial measurement unit ("IMU"), electromyography sensor, neuromuscular, fatigue, orthotic, and lower extremity are meant to include or encompass all equivalents for such elements. Such equivalents are contemplated for each element named herein.

For purposes of summarizing, certain aspects, advantages and novel features of the present invention are provided herein. It is to be understood that not all such aspects, advantages, or novel features may be provided in any one particular embodiment. Thus, the disclosed subject matter may be embodied or carried out in a manner that achieves or optimizes one aspect, advantage, or novel feature or group of features without achieving all aspects, advantages, or novel features as may be taught or suggested.

In view of the foregoing disadvantages inherent in the known art, the present invention relates to a more effective means and method to identify correlating physiological factors involved in internal and external joint work to determine how efficiently a person maintains neuromuscular stability of the lower extremities within a certain environment (i.e. an orthotic, shoe, brace, or prosthetic). The general purpose of the invention, which will be described subsequently in greater detail, is to measure and reduce the risk of lower extremity injury.

The features of the invention which are believed to be novel are particularly pointed out and distinctly claimed in the concluding portion of the specification. By way of non-limited example, the present invention provides a novel means and method to identify correlating physiological factors involved in internal and external joint work to determine how efficiently a person maintains neuromuscular stability of the lower extremities within a certain environment (i.e. an orthotic, shoe, brace, or prosthetic). These and other features, aspects, and advantages of the present invention will become better understood with reference to the following drawings and

DETAILED DESCRIPTION

The present invention addresses the prediction of lower extremity injury. By utilizing IMUs, computer vision, EMG sensors and a novel injury prediction algorithm, individuals are able to identify primary correlating physiological factors involved in internal and external joint work to determine measure the risk of lower extremity injury.

In accordance with an aspect of the present invention, a muscle activity correlation method is provided for calculating the ground reaction force used to find both the force and the torque at the ankle as observed by the following equation $$F_G = \frac{M_a}{MVC} * W$$

wherein $M_G$ is the muscle activity read by the EMG, MVC is the maximum volatile contraction measured before the assessment, and W is the weight of the individual subject.

In accordance with another aspect of the present invention, the muscle activity correlation method calculates the torque of an individual subject's ankle. The method involves using the positional information from the IMU and the muscle activity or contraction measured by the EMG by first establishing a relationship between the muscle activity and the reaction force from the ground. The summing analysis of the torque forces at play in an individual subject's ankle, factoring the IMU in relation to the ground point of contact, the ankle joint, and the center of mass of the foot, is observed by the following:

$$\vec{F}_A = [m(\vec{a}_{s1} + \vec{\omega}_1 \times \vec{r}_{c1/s1} + \vec{\omega}_1 \times (\vec{\omega}_1 \times \vec{r}_{c1/s1}))] - \vec{F}_G$$

wherein m is the mass of the foot, $\omega_1$ is the angular acceleration vector of the foot, $r_{c1/s1}$ is the vector pointing from the IMU to the foot's center of mass, $a_{s1}$ is the angular acceleration vector of the sensor, and $F_G$ is the ground reaction force vector.

In accordance with another aspect of the present invention, a muscle activity correlation method is provided for calculating the moment stability at the individual subject's ankle by utilizing the force vector as observed by the following equation $$\vec{M}_A + \vec{M}_G = \Sigma \vec{M}_{c1} = J_1 \vec{\omega}_1 - \vec{r}_{c1/G} \times \vec{F}_G - \vec{r}_{c1/A} \times \vec{F}_A$$

wherein $M_A$ is the moment vector of the ankle, $M_G$ is the moment vector of the contact point between the ground and the foot, $J_1$ is the inertia tensor of the foot about its center of mass, and $r_{c1/G}$ and $r_{c1/A}$ represent the vector pointing from the contact point of the ground to the center of mass of the foot and the vector pointing from the ankle to the center of mass of the foot respectively. This aspect of the present invention assumes that Mc is zero as there is no opposition to the motion at the contact point between the ground and the foot.

In accordance with a further aspect of the present invention, the data from the IMU and EMG sensors are measured simultaneously as the MVC is aligned with the frequency of readings between the IMU and the EMG sensors.

BRIEF DESCRIPTION OF THE DRAWINGS

Those of skill in the art will understand that the drawings, described below, are for illustrative purposes only. The drawings are not intended to limit the scope of the present teachings in any way.

DETAILED DESCRIPTION OF THE INVENTION

Abbreviations and Definitions

Figure 1:
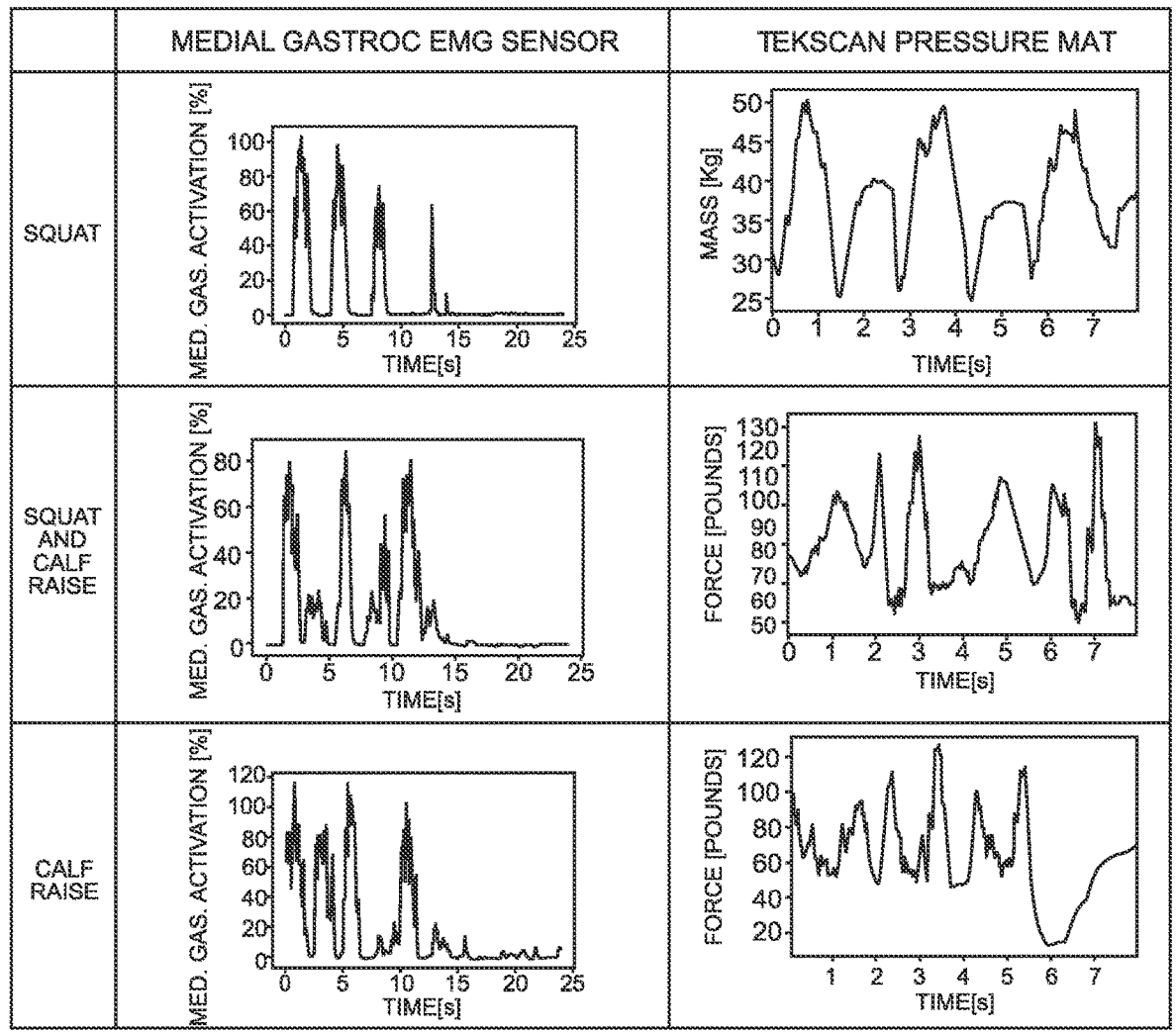
FIG. 1 is a graphical representation of data collected in the course of a first experiment on at least one embodiment of the present invention.

IMU: as used herein and traditionally in the industry of the art, the term "IMU" refers to an inertial measurement unit which is an electronic device that measures and reports a body's specific force, angular rate, and sometimes the orientation of the body, using a combination of accelerators, gyroscopes, and sometimes magnetometers. IMU may also be referenced as movement/motion capturing technology.

EMG: as used herein, the term "EMG" or "Electromyography" refers to an electrodiagnostic medicine technique used for evaluating and recording the electrical activity produced by skeletal muscles, which is performed using an instrument called an electromyograph.

Sensors: as used herein, the term "sensors" may be used interchangeably with IMU and EMG (i.e., IMU sensor or EMG sensor) and refers to a device that measures small electrical signals generated by an individual subject's muscles when the muscles are moved, such as when an individual subject engages in a muscle activity.

Pressure Mat: as used herein, the term "pressure mat" refers to a device that measures the pressure distribution between any two mating or contacting surfaces. As used herein, the pressure mat is used to measure the plantar pressure and forces an individual subject exudes during a specified muscle activity.

Plantar Pressure: as used herein, the term "plantar pressure" refers to the pressure field that acts between the foot and the foot's support surface during a specified muscle activity.

Concentric Contraction: as used herein, the term "concentric contraction" refers to a type of muscle activation that causes tension on an individual subject's muscle while it shortens (or contracts) with the requisite muscle movement.

Statistical Analysis Software: as used herein, the term "statistical analysis software" refers to tools that assist in the statistic-based collection and analysis of data to provide science-based insights into patterns and trends.

Ground Reaction Force: as used herein, the term "ground reaction force" is the force acting in the opposite direction of the action. By way of example, when someone jumps, s/he exerts a downward reaction force on the ground as s/he pushes off the ground and leaps into the air.

Parity Plot: as used herein, the term "parity plot" refers to a scatterplot graph that compares experimental data against tabulated data wherein "x" is the tabulated data and "y" is the corresponding experimental value.

Movement Mapping: as used herein, the term "movement mapping" refers to the correlation between muscle movement and a specified activity.

Neuromuscular Stability: as used herein, the term "neuromuscular stability" refers to the recurrent peripheral nervous system formation of a stereotyped pattern of muscle contractions that are primarily used to provide steadiness to the skeletal system in opposition of gravity. By way of example, human posture, which is the static and dynamic varying erect position of the musculoskeletal system, is the direct result of consistent "neuromuscular stability" powered by the peripheral nervous system.

Numeric Representation: as used, herein, the term "numeric representation" refers to the quantitative values directly associated with the muscle activity or neuromuscular measurement of the physiological variable collected from the associated vectors related to said muscle activity.

Medial Gastrocnemius or Gastrocnemius Muscle: as used herein, the term "medial gastrocnemius muscle" refers to the medial head of the gastrocnemius muscle located in the back part of the lower leg of a human being, running from the knee to the heel, otherwise known as the collective "calf muscle". As referenced herein, the medial gastrocnemius muscle has a greater risk of injury than the lateral head of the gastrocnemius muscle.

Calf Raise: as used herein, the term "calf raise" is a method of exercising the gastrocnemius muscle, tibialis posterior, peroneal and soleus muscles of the lower leg. As referenced herein, the specific movement performed is a plantar flexion or ankle extension.

Computer Vision or Computer Vision Technology: as used herein, the term "computer vision" or "computer vision technology" is an interdisciplinary scientific filed that deals with how computers can gain high-level understanding from digital images or videos and utilize input data to predict a specified outcome. Computer Vision Technology may also be referenced as movement/motion capturing technology.

As used herein, words and terms referring to a bone, muscle, or tendon located in the lower extremity of the body shall have their ordinary meaning, as known in the field of the art.

The present invention overcomes the limitations of the prior art by providing a new and more effective means to determine how efficiently a person maintains neuromuscular stability of the lower extremities within a certain environment (i.e. an orthotic, shoe, brace, or prosthetic) to measure and reduce the risk of lower extremity injury.

All dimensions specified in this disclosure are by way of example only and are not intended to be limiting. Further, the proportions shown in these Figures are not necessarily to scale. As will be understood by those with skill in the art with reference to this disclosure, the actual dimensions and proportions of any embodiment or element of an embodiment disclosed in this disclosure will be determined by its intended use.

It is to be understood that the drawings and the associated descriptions are provided to illustrate potential embodiments of the invention and not to limit the scope of the invention. Reference in the specification to "one embodiment" or "an embodiment" is intended to indicate that a particular feature, structure, or characteristic described in connection with the embodiment is included in at least an embodiment of the invention. The appearances of the phrase "in one embodiment" or "an embodiment" in various places in the specification are not necessarily all referring to the same embodiment.

Throughout the drawings, reference numbers are reused to indicate correspondence between referenced elements. In addition, the first digit of each reference number indicates the figure where the element first appears.

As used in this disclosure, except where the context requires otherwise, the term "comprise" and variations of the term, such as "comprising", "comprises" and "comprised" are not intended to exclude other additives, components, integers or steps.

In the following description, specific details are given to provide a thorough understanding of the embodiments. However, it will be understood by one of ordinary skill in the art that the embodiments may be practiced without these specific details. Well known features, elements or techniques may not be shown in detail in order not to obscure the embodiments.

Aspects of the present teachings may be further understood in light of the following examples, which should not be construed as limiting the scope of the present teachings in any way.

The premise for this research is that conventional means to ascertain the risk of lower extremity injury do not efficiently determine how a person maintains neuromuscular stability within a certain environment.

The experimental results, disclosed generally herein, are conducted to test potential methods to accurately, adequately, and efficiently measure the risk of a lower extremity injury in a targeted individual.

DETAILED DESCRIPTION OF THE INVENTION

The present invention discloses a method and system for detecting the risk of lower body extremity injuries and reducing the risk of the same. Independent and dependent variables attribute to the range of an individual subject's muscle movement and, in turn, the potential for risk of lower body extremity injury. The independent variables may include an individual subject's weight and muscular composition. The dependent variables may be the selected physical activity or the selected time interval each muscle activity is performed.

The present invention identifies the correlation between independent and dependent variables of muscle activity ("Muscle Activity Correlation"). Specifically, Muscle Activity Correlation identifies the primary correlating physiological factors involved in internal and external joint work to determine the measure of risk of lower extremity injury an individual subject may have.

The analysis of the independent and dependent variables that impact the Muscle Activity Correlation is achieved by first calculating the ground reaction force in response to a specified muscle activity. The calculation of the ground reaction force identifies both the force and the torque at the ankle during a specified muscle activity $$F_G = \frac{M_a}{MVC} * W$$

wherein $M_G$ is the muscle activity read by the EMG, MVC is the maximum volatile contraction measured before the assessment, and W is the weight of the individual subject In a preferred embodiment of the present invention, an individual subject's muscle movement and activity are observed in a controlled environment allowing for the determination of the individual subject's joint displacement of joint(s) affixed to a muscle and/or muscle group of interest during a controlled and specified muscle activity.

The summing analysis of the torque forces at play in an individual subject's ankle, factoring the IMU in relation to the ground point of contact, the ankle joint, and the center of mass of the foot determines the joint displacement of a joint(s) affixed to a muscle and/or muscle group of interest during a specified muscle activity, and can be observed by the following:

$$\vec{F}_A = [m(\vec{a}_{s1} + \vec{\omega}_1 \times \vec{r}_{c1/s1} + \vec{\omega}_1 \times (\vec{\omega}_1 \times \vec{r}_{c1/s1}))] - \vec{F}_G$$

wherein m is the mass of the foot, $\omega_1$ is the angular acceleration vector of the foot, $r_{c1/s1}$ is the vector pointing from the IMU to the foot's center of mass, $a_{s1}$ is the angular acceleration vector of the sensor, and $F_G$ is the ground reaction force vector. Joint displacement is determined by the IMU and movement capturing technology, whereby the IMU and/or movement capturing technology measures the orientation of the skeletal frame and body movement during a specified muscle activity. Specifically, the orientation of the skeletal frame is determined by the specific force, angular rate, and skeletal position during a specified muscle activity.

The Muscle Activity Correlation also determines an individual subject's neuromuscular effort during a specified muscle activity along with the neuromuscular stability of a muscle and/or muscle group of interest and the joint displacement, which measures an individual subject's risk for lower extremity injury.

The moment vector of the ankle $M_A$ and the moment vector of the contact point between the ground and the foot $M_G$, combined with the ground reaction force data $F_G$ are used to determine an individual subject's neuromuscular effort by calculating the moment stability at the individual subject's ankle by utilizing the force vector $$\vec{M}_A + \vec{M}_G = \Sigma \vec{M}_{c1} = J_1 \vec{\omega}_1 - \vec{r}_{c1/G} \times \vec{F}_G - \vec{r}_{c1/A} \times \vec{F}_A$$

wherein $M_A$ is the moment vector of the ankle, $M_G$ is the moment vector of the contact point between the ground and the foot, $J_1$ is the inertia tension of the foot about its center of mass, and $r_{c1/G}$ and $r_{c1/A}$ represent the vector pointing from the contact point of the ground to the center of mass of the foot and the vector pointing from the ankle to the center of mass of the foot respectively. This aspect of the present invention assumes that $M_G$ is zero as there is no opposition to the motion at the contact point between the ground and the foot.

Neuromuscular effort takes into consideration the eccentric and concentric work of a muscle and/or muscle group of interest during a specified muscle activity.

As shown in FIG. 1, Muscle Activity Correlation readings are observed during specified activity sets during specified time intervals while an individual subject was utilizing a commercial pressure mat and while an individual subject is connected to EMGs. The Muscle Activity Correlation readings represented in FIG. 1 identify eccentric and concentric contraction data collected from an individual subject as the individual subject is standing on a commercial pressure mat while EMG sensors are simultaneously connected to the center of the individual subject's tibialis anterior and the center of the individual subject's medial and lateral gastrocnemius. The outputs of the pressure mat readings and the EMG readings, as shown in FIG. 1, are displayed as the percentages of the user's standing force data, or ground reaction force data.

Figure 2A:
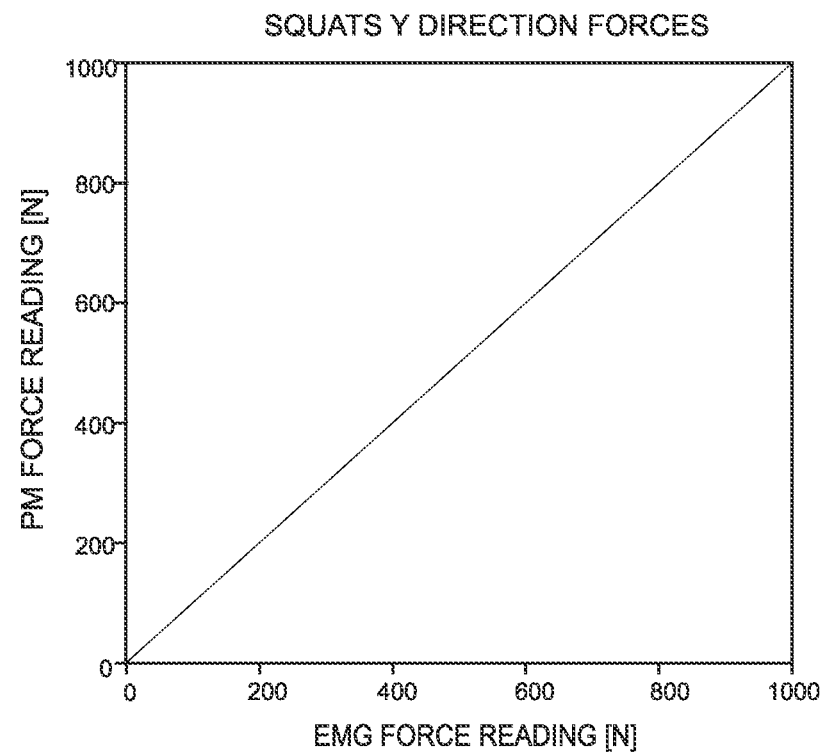
FIG. 2A is a graphical representation of data collected in the course of a first experiment on at least one embodiment of the present invention.
Figure 2B:
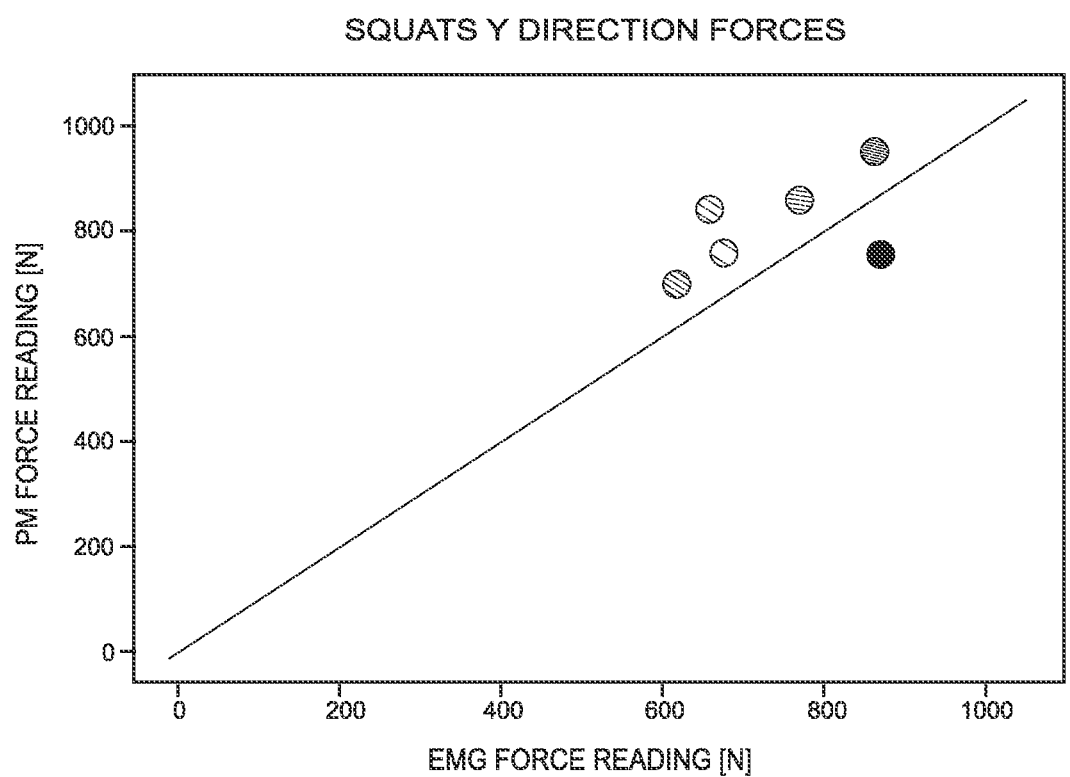
FIG. 2B is a graphical representation of data collected in the course of a first experiment on at least one embodiment of the present invention.

As can be seen in FIG. 2A and FIG. 2B, the force data outputs from the pressure mat and the EMG are compared against an individual subject's squat movements and calf raise movements. In the graphical representations shown, the X-axis is the ground reaction force calculated using the muscle activity of the medial gastrocnemius (measured by the maximum volatile contraction) and the weight of the individual subject, whereby the Y-axis is the ground reaction force measurement using the pressure mat. When compared using a parity plot, the force outputs from the pressure mat and EMG show that the similarity between predictions for calf raises is much higher due to the measurement of the main muscle used to perform a calf raise (the medial gastrocnemius) and a lessened influence from other muscle groups such as peroneus longus, posterior tibialis, tibialis anterior, as depicted in FIG. 2B.

The correlation between force fractions and muscle activity, in that when muscle activity occurs during a specific movement, such as a calf raise, plantar pressure also increases may be seen in FIG. 1, FIG. 2A, FIG. 2B, and may be summarized as identifying an individual subject's neuromuscular effort.

Figure 3A:
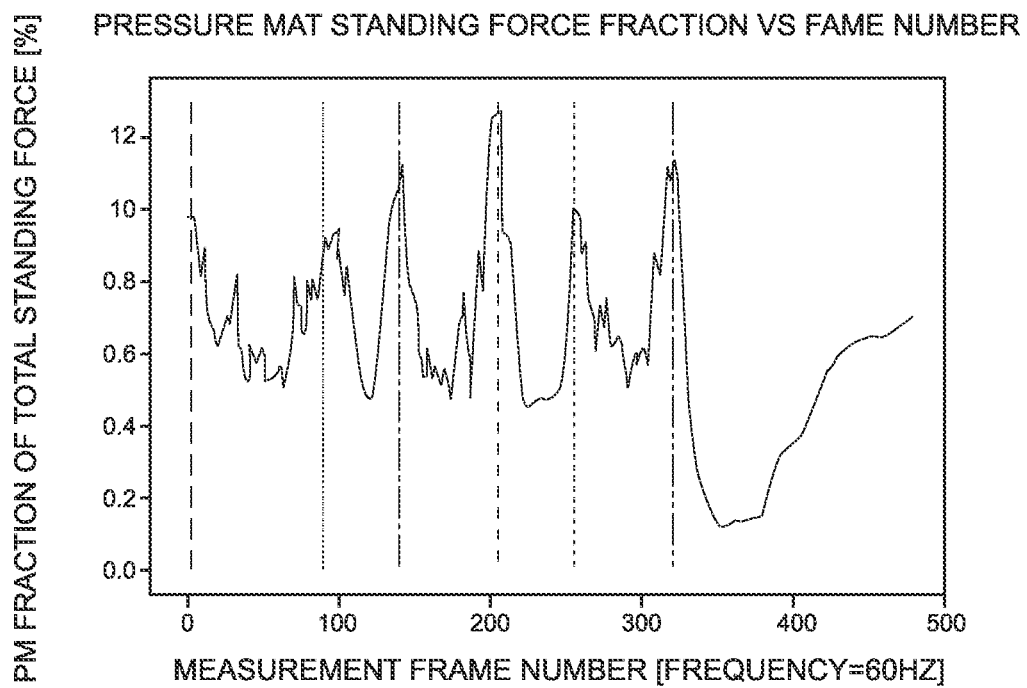
FIG. 3A is a graphical representation of data collected in the course of a first experiment on at least one embodiment of the present invention.
Figure 3B:
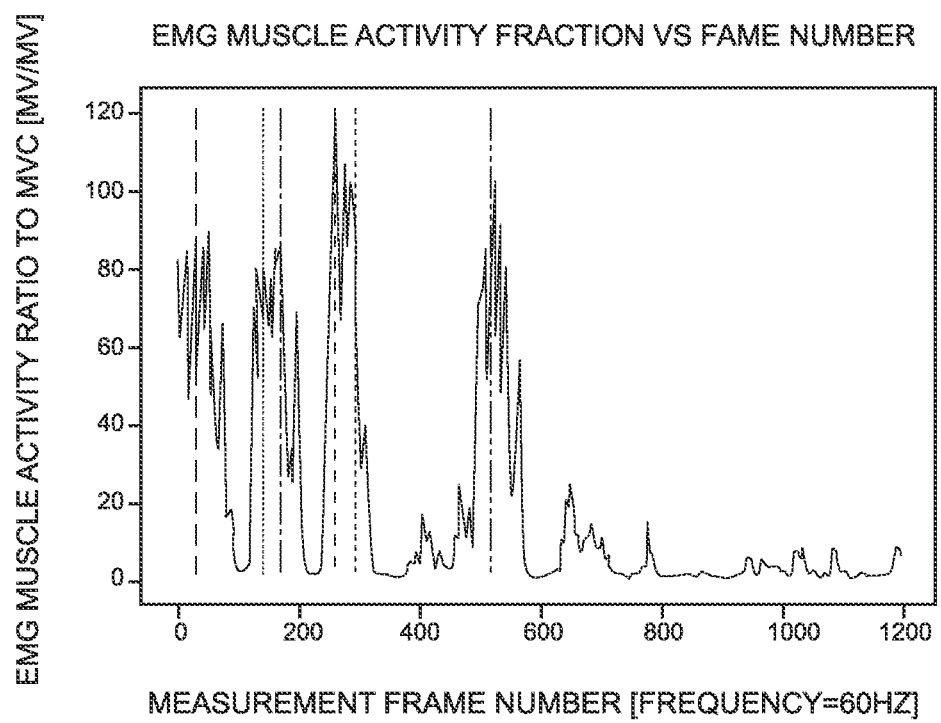
FIG. 3B is a graphical representation of data collected in the course of a first experiment on at least one embodiment of the present invention.

Turning attention to FIG. 3A and FIG. 3B, a graphically representation of the device peak readings of FIG. 2B is shown. A viewer may perceive that FIG. 3A shows the full weight fraction data set obtained by the pressure mat, while FIG. 3B depicts the full weight fraction data set obtained by the EMG during the duration of the specified movement. A viewer may also perceive that the vertical lines in the device peak readings of FIG. 3A and FIG. 3B mark the locations of peaks calculated by the statistical analysis software. More specifically, the peaks of FIG. 3A represent instances where the individual subject is standing at rest in between one full repetition of movement, whereas the peaks of FIG. 3B represent instances where the individual subject was at the highest position of the calf raise.

Figure 4A:
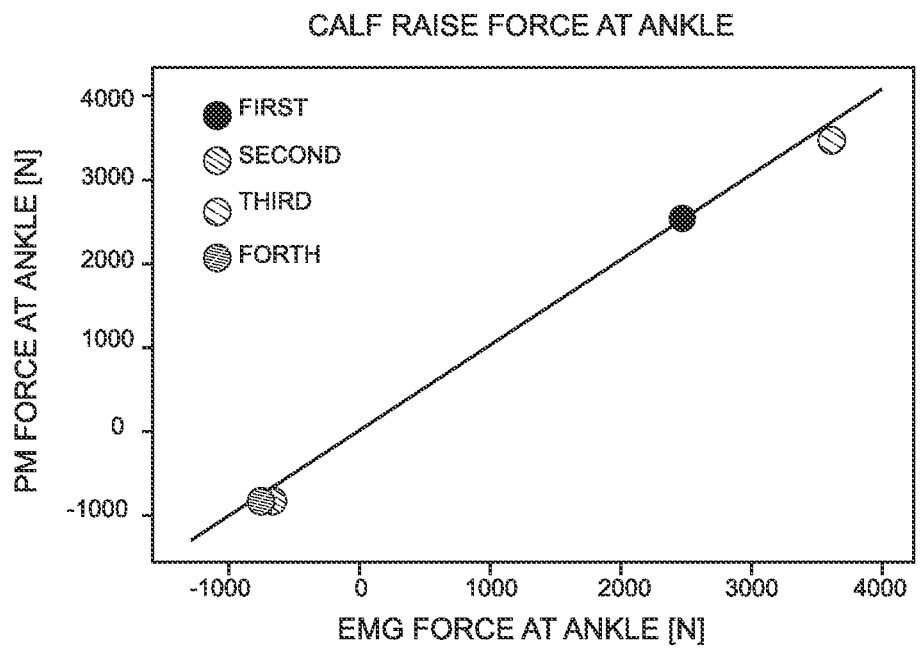
FIG. 4A is a graphical representation of data collected in the course of a first experiment on at least one embodiment of the present invention.
Figure 4B:
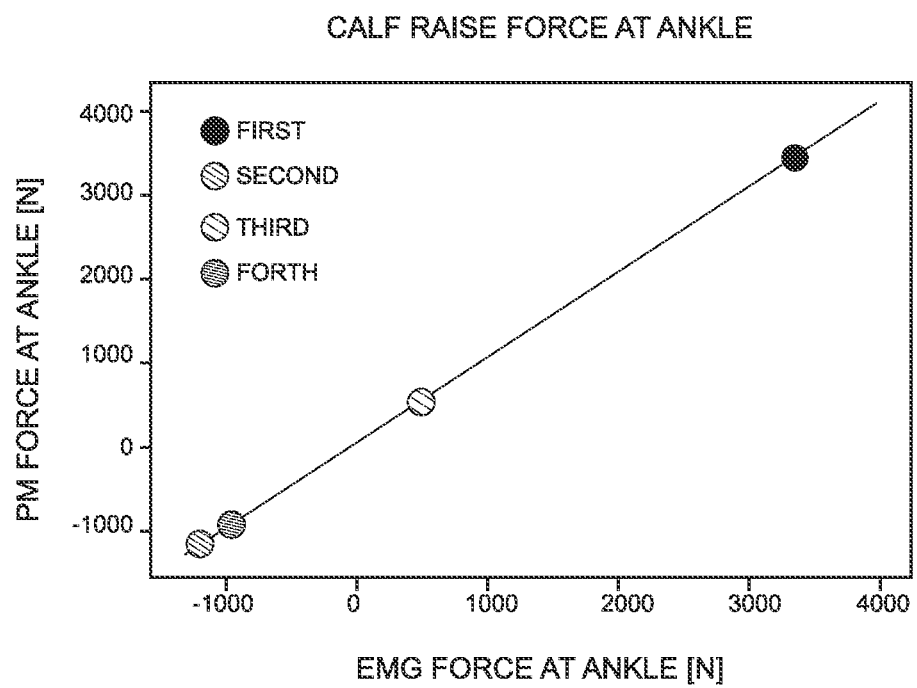
FIG. 4B is a is a graphical representation of data collected in the course of a first experiment on at least one embodiment of the present invention.
Figure 5A:
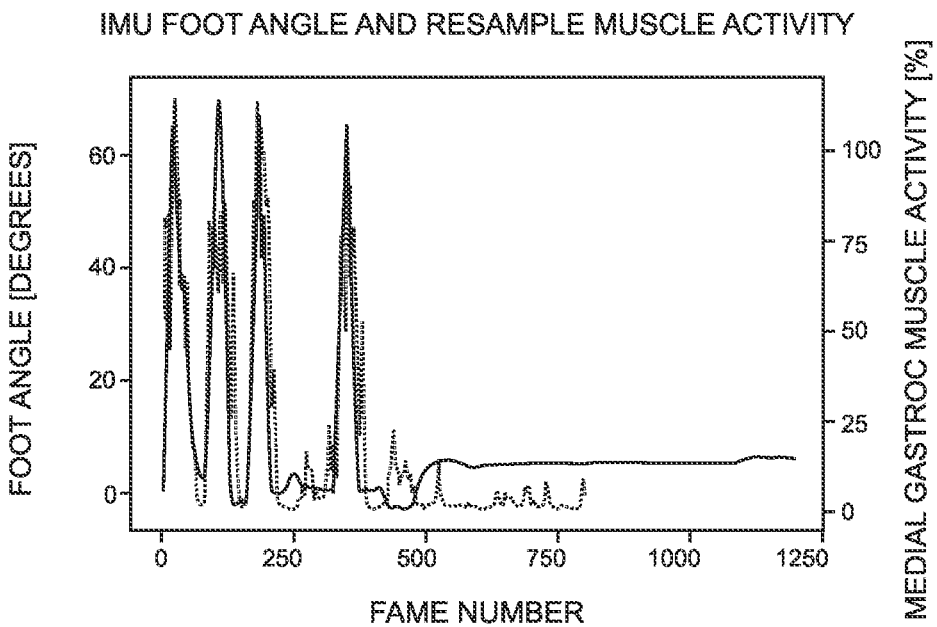
FIG. 5A is a graphical representation of data collected in the course of a second experiment on at least one embodiment of the present invention.
Figure 5B:
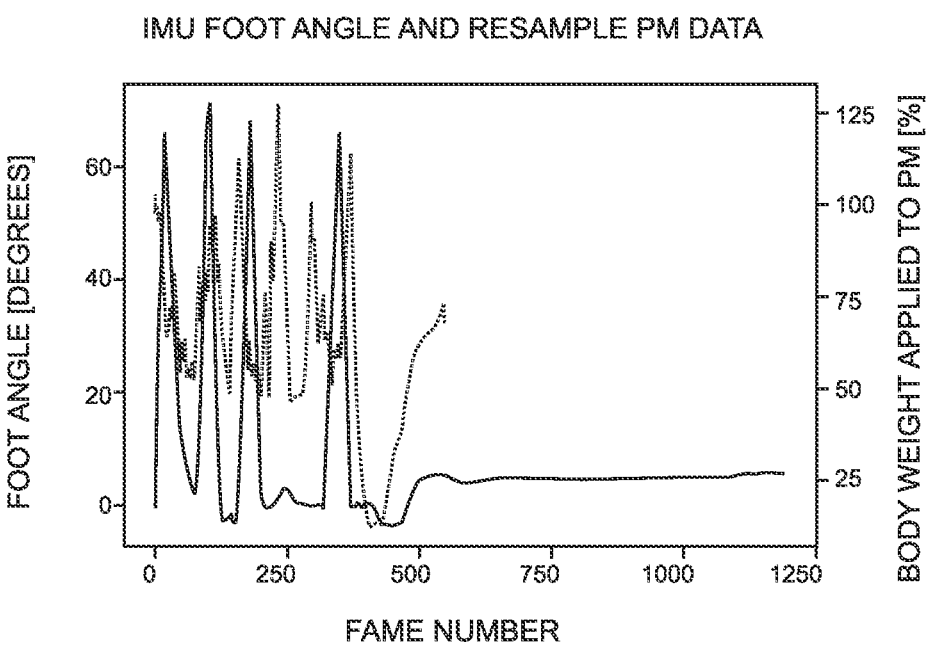
FIG. 5B is a graphical representation of data collected in the course of a second experiment on at least one embodiment of the present invention.

Torque is the rate of change that the joint will experience as related to the muscle contraction and force that is generated under the foot. In the embodiments depicted in FIGS. 4A and 4B, the y-axis shows torque values calculated using ground force reaction forces measured by the pressure mat. The x-axis torque is calculated in the same manner as the y-axis, however, the ground reaction force is calculated using the muscle activity of the individual user's medical gastrocnemius and the individual user's weight.

Where FIG. 1, FIGS. 2A and 2B, FIGS. 3A and 3B, and FIGS. 4A and 4B depict the accuracy of determining an individual subject's neuromuscular effort using EMG calculations as opposed to a commercial pressure mat, FIGS. 5A and 5B depict an individual subject's neuromuscular stability.

Neuromuscular stability is determined by analyzing the vector computations of $\vec{M}_A$, $\vec{M}_G$, and $\vec{F}_A$ derived from specified muscle activities. The analysis of an individual subject's neuromuscular effort and neuromuscular stability (collectively, "Movement Mapping Analysis"), identifies the specific movement that creates the greatest potential risk of injury to an individual subject. The data also evidences the threshold of muscle fatigue and risk of injury.

As depicted in FIGS. 5A and 5B, the positional data from the IMU along with the muscle activity or contraction measured by the EMG establishes a relationship between the muscle activity and the reaction force from the ground.

To strengthen the correlation between force fractions and muscle activity, and as an interchangeable alternative IMUs, computer vision algorithms (collectively "Movement Capturing Technology") are utilized to capture, process, and analyze visual data associated with the individual subject's movement during defined exercises and physical objectives.

Figure 6:
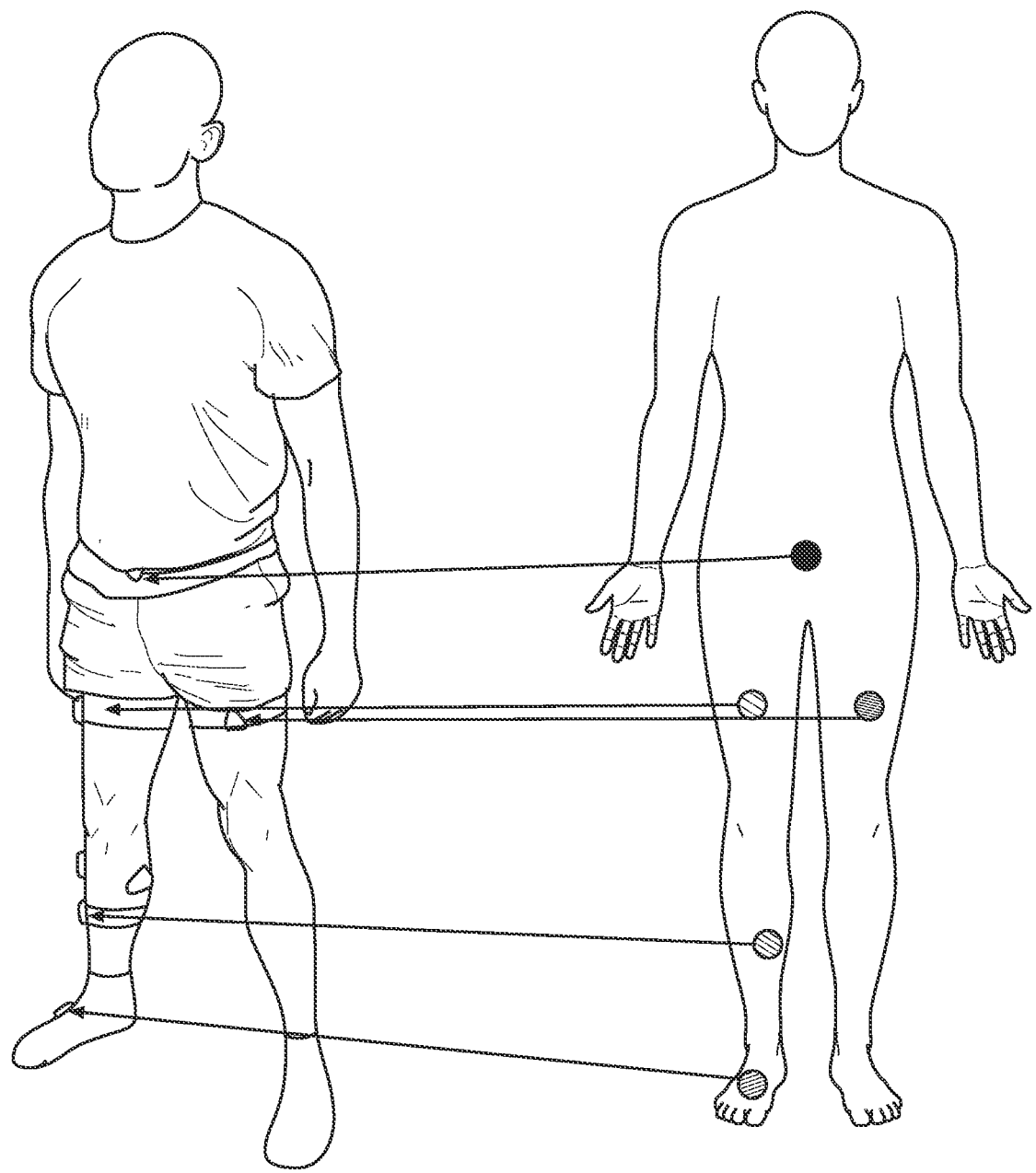
FIG. 6 is a perspective view of at least one embodiment of the present invention.

Individually, both EMG and Movement Capturing Technology provide an individual subject the means to receive immediate feedback of neuromuscular effort and neuromuscular stability. As depicted in FIG. 6 when IMU sensors are placed on the torso, lower hip, left and right thigh, left and right ankle, and left and right shin, and where EMG sensors are simultaneously placed on the right and left medial gastrocnemius as well as the right and left lateral gastrocnemius of the individual subject, the sensors work in tandem to determine the real time displacement between each joint during an isolated neuromuscular effort or series of neuromuscular efforts.

Figure 7:
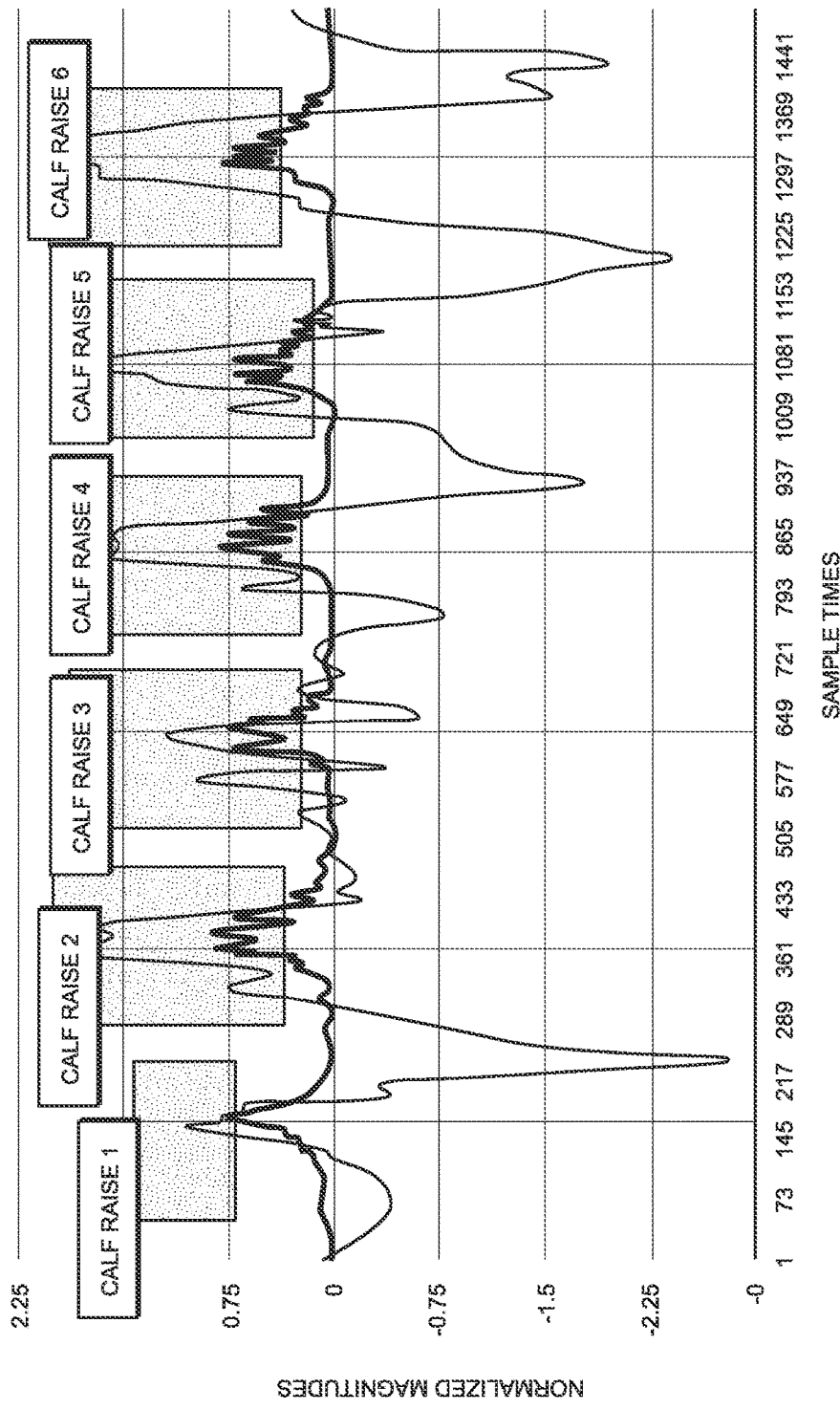
FIG. 7 is a graphical representation of data collected in the course of a third experiment on at least one embodiment of the present invention.

In a preferred embodiment of the present invention, the fusion of the EMG and IMU sensors provide accurate body and muscle position readings, as well as isolated neuromuscular effort, in a single signal as may be seen in FIG. 7 as evidence that muscle effort and the pressure amount of force increase at the same time and at the same rate, respectively.

In the embodiment illustrated by FIG. 7 the fusion of an EMG with a movement capturing technology, such as an IMU, ("Sensor Fusion") results in consistent peak amplitudes of accuracy across a multitude of sample data. The Sensor Fusion also allows for skeletal tracking (not shown) of an individual subject's motions, joints, and limbs.

In a preferred embodiment of the present invention, the data derived from the vector computations of $\vec{M}_A$, $\vec{M}_G$, and $\vec{F}_A$ derived from specified muscle activities are assigned numerical values to determine a baseline numerical representation based on the neuromuscular stability. This predictive computer model is generated and customized to determine a threshold of neuromuscular effort, joint displacement, and neuromuscular stability of a select muscle and/or muscle group of interest which, in turn, determines the probability of risk of neuromuscular injury within a pre-determined scope of muscle activities.

The predictive computer model is further customized to analyze the divergence between the baseline numeric representation of an individual subject against additional data points derived from neuromuscular effort, joint displacement, or neuromuscular stability to generate specified muscle activity criteria to reduce the probability of risk of neuromuscular injury within a pre-determined scope of muscle activities. By creating a machine learning predictive computer model which generates the probability of risk of neuromuscular injury and muscle activity criteria to reduce said risk without the aid of EMG sensors, the present invention is distinguished from the prior art which relies on the continuous use of EMG sensors to rate and/or determine the risk of neuromuscular injury.

Figure 8:
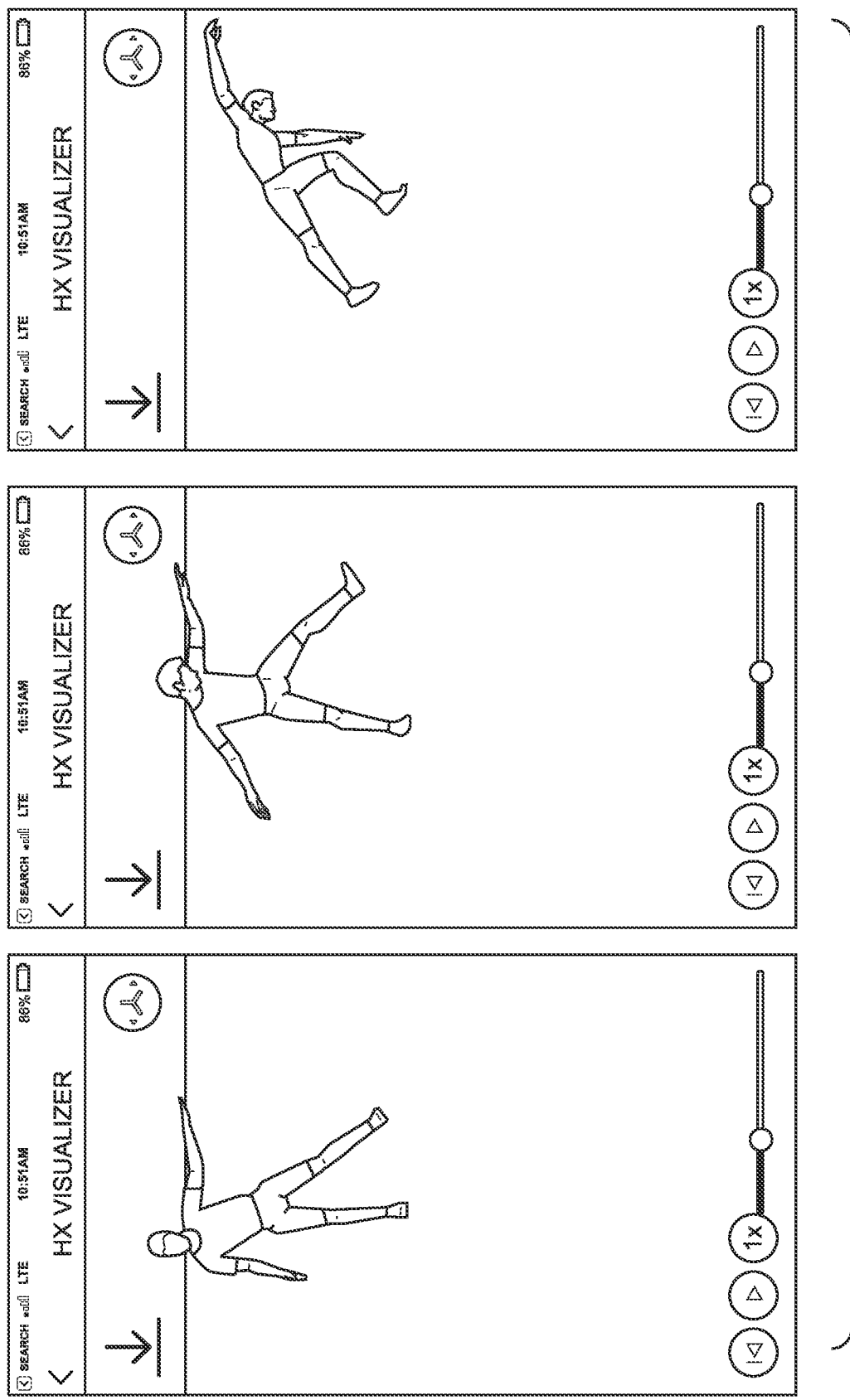
FIG. 8 is a schematic view of at least one embodiment of the present invention.

In another preferred embodiment, skeletal tracking data readings from the Sensor Fusion allow the algorithms of the present invention to predict muscle movement and risk of injury based on an individual subject's prior Sensor Fusion data readings and joint displacement data. This data, when used in conjunction with a mobile application, as depicted by FIG. 8 may then allow the individual subject to determine specialized algorithmic-based exercises and activities that would reduce the risk of injury for the individual subject. These algorithmic-based exercises represent the optimized movements for the individual subject based on the data presented.

CONCLUSIONS, RAMIFICATIONS, AND SCOPE

Although the present invention has been described with a degree of particularity, it is understood that the present disclosure has been made by way of example and that other versions are possible. As various changes could be made in the above description without departing from the scope of the invention, it is intended that all matter contained in the above description or shown in the accompanying drawings shall be illustrative and not used in a limiting sense. The spirit and scope of the appended claims should not be limited to the description of the preferred versions contained in this disclosure.

All features disclosed in the specification, including the claims, abstracts, and drawings, and all the steps in any method or process disclosed, may be combined in any combination, except combinations where at least some of such features and/or steps are mutually exclusive. Each feature disclosed in the specification, including the claims, abstract and drawings, can be replaced by alternative features serving the same, equivalent or similar purpose, unless expressly stated otherwise. Thus, unless expressly stated otherwise, each feature disclosed is one example only of a generic series of equivalent or similar features.

Any element in a claim that does not explicitly state "means" for performing a specified function or "step" for performing a specified function should not be interpreted as a "means" or "step" clause as specified in 35 U.S.C. § 112.

While the present invention has been disclosed in connection with a number of embodiments shown and described in detail, various modifications should be readily apparent to those of skill in the art.

What is claimed is:

1. A method for detecting a risk of lower body extremity injuries in a subject, the method comprising the steps of:
    (a) measuring a joint displacement value of at least one joint affixed to a specified muscle during a specified muscle activity;
    (b) calculating, from one or more moment vectors and ground reaction force data, a neuromuscular effort value of the specified muscle during the specified muscle activity;
    (c) calculating, from one or more moment vectors and ankle torque force data, a neuromuscular stability value of the at least one joint and the specified muscle; and
    (d) determining, from (i) the joint displacement value, (ii) the neuromuscular effort value and (iii) the neuromuscular stability, a numeric representation of risk of the at least one joint affixed to the specified muscle, wherein the numeric representation of risk is associated with the risk of lower body extremity injury.

2. The method of claim 1, wherein the neuromuscular effort value is determined from a measurement from at least one sensor wherein the at least one sensor measures one or more of an eccentric work and a concentric work of the specified muscle.

3. The method of claim 2, wherein each of the eccentric work and concentric work of the specified muscle is determined from an electric potential generated by the specified muscle during the specified muscle activity.

4. The method of claim 1, wherein the joint displacement value is determined using a measurement from at least one sensor, wherein the at least one sensor determines an orientation of the subject's skeletal frame and a body movement during the specified muscle activity.

5. The method of claim 4, wherein the orientation is determined using a calculation of a specific force, an angular rate, and a skeletal position during the specified muscle activity.

6. The method of claim 4, wherein the at least one sensor is a motion capturing device.

7. The method of claim 1, wherein the one or more moment vectors and ankle torque force data used to determine the neuromuscular stability are determined using a series of vector computations associated with the specified muscle activity.

8. The method of claim 1, wherein the neuromuscular effort value, joint displacement value, and neuromuscular stability are determined using a series of vector computations associated with the specified muscle activity.

9. The method of claim 1, wherein the neuromuscular effort value, joint displacement value, and neuromuscular stability of a specified muscle are generated as at least one sequence of data, wherein the sequence of data may be maintained in a historical database.

10. The method of claim 1, wherein a difference between the numeric representation of risk comprising the neuromuscular effort value, joint displacement value, and neuromuscular stability of the specified muscle and a numeric representation determined from at least one other source of data is computed, wherein the at least one other source of data comprises one or more of a neuromuscular effort value, a joint displacement value, and a neuromuscular stability related to the at least one specified muscle activity and obtained from one or more other subjects.

11. The method of claim 10, wherein the difference between a) the numeric representations of risk obtained from the subject, and b) the one or more other sources of data for a specified muscle is used to determine a probability of risk of a lower body extremity injury comprising a neuromuscular injury for the specified muscle activity.

12. The method of claim 11, wherein the probability of risk of neuromuscular injury is determined when the difference exceeds a threshold value.

13. A system for detecting a risk of lower body extremity injuries, the system comprising:
    one or more processors; and
    a data store coupled to the one or more processors, having instructions stored thereon, wherein when executed by at least one of the or more processors, causes the one or more processors to perform one or more operations comprising:
    measuring a joint displacement value for at least one joint affixed to a specified muscle during a specified muscle activity;
    calculating, from one or more moment vectors and ground reaction force data, a neuromuscular effort value for the specified muscle during the specified muscle activity;
    calculating, from one or more moment vectors and ankle torque force data, a neuromuscular stability of the at least one joint and the specified muscle based on the determined joint displacement value and the determined neuromuscular effort value;
    generating a numeric representation for the joint(s) and the specified muscle, and
    assigning a risk value to the generated numeric representation wherein the risk value is associated with a risk for a lower body extremity injury.

14. The system of claim 13, wherein the numeric representation for the specified muscle is generated as at least one sequence of data, wherein the at least one sequence of data is stored in a historical database.

15. The system of claim 14, wherein the system is configured to assign a classification to the at least one sequence of data, and the system is respectively trained to use the at least one sequence of data as a training data set.

16. The system of claim 13, wherein the system is configured to compute a difference between the numeric representation and a second set of at least one other sequence of data, wherein the second set of at least one other sequence of data comprises a numeric representation based on a neuromuscular effort value, a joint displacement value, or neuromuscular stability related to at least one specified muscle activity.

17. The system of claim 16, wherein the system analyzes the computed difference between the numeric representation and the second set of at least one other sequence of data, and generates a muscle activity criteria for reducing probability of risk based on the computed difference.

18. The system of claim 17, wherein the generated muscle activity criteria comprises a guidance for muscle activity values to reduce the risk of a lower body extremity injury comprising a neuromuscular injury.

19. A non-transitory computer-readable medium storing program that causes a processor to:

receive a joint displacement data of at least one joint affixed to a specified muscle during a specified muscle activity;

receive a neuromuscular effort data calculated from one or more moment vectors and ground reaction force data of the specified muscle during the specified muscle activity;

determine, using one or more moment vectors and ankle torque force data, a neuromuscular stability of the at least one joint and the specified muscle based on the received joint displacement data and the received neuromuscular effort data; and generate a numeric representation of the neuromuscular stability of the at least one joint and the specified muscle, wherein the numeric representation is associated with a risk for lower body extremity injury.

20. The non-transitory computer-readable medium of claim 19, wherein the numeric representation of the neuromuscular stability of the at least one joint and the specified muscle is received as at least one sequence of data, wherein the sequence of data is maintained in a historical database.

* * * * *